United States Patent
Wiget et al.

(10) Patent No.: US 9,801,967 B2
(45) Date of Patent: Oct. 31, 2017

(54) SATURATION-ENHANCED, LOW-CONCENTRATION VAPORIZED HYDROGEN PEROXIDE DECONTAMINATION METHOD

(71) Applicant: STERIS INC., Temecula, CA (US)

(72) Inventors: Paul A Wiget, Mentor, OH (US); Timothy W Meilander, Broadview Heights, OH (US); Iain McVey, Lakewood, OH (US)

(73) Assignee: STERIS INC., Temecula, CA (US)

( * ) Notice: Subject to any disclaimer, the term of this patent is extended or adjusted under 35 U.S.C. 154(b) by 0 days.

(21) Appl. No.: 14/660,233

(22) Filed: Mar. 17, 2015

(65) Prior Publication Data

US 2015/0265738 A1 Sep. 24, 2015

Related U.S. Application Data

(60) Provisional application No. 61/955,283, filed on Mar. 19, 2014.

(51) Int. Cl.
*A61L 2/20* (2006.01)
*A61L 2/07* (2006.01)

(52) U.S. Cl.
CPC .............. *A61L 2/208* (2013.01); *A61L 2/07* (2013.01); *A61L 2202/122* (2013.01)

(58) Field of Classification Search
CPC . A61L 2/20; A61L 2/202; A61L 2/206; A61L 2/208
See application file for complete search history.

(56) References Cited

U.S. PATENT DOCUMENTS

| | | | |
|---|---|---|---|
| 3,609,296 A * | 9/1971 | Blair | B01J 3/044 165/10 |
| 4,169,123 A | 9/1979 | Moore et al. | 422/29 |
| 4,169,124 A | 9/1979 | Forstrom et al. | 422/33 |
| 4,642,165 A | 2/1987 | Bier | 203/12 |
| 4,909,999 A | 3/1990 | Cummings et al. | 422/298 |
| 4,956,145 A | 9/1990 | Cummings et al. | 422/28 |
| 5,173,258 A | 12/1992 | Childers | 422/27 |

(Continued)

FOREIGN PATENT DOCUMENTS

| | | | |
|---|---|---|---|
| WO | WO 2008/014615 WO | 2/2008 | A61L 2/20 |
| WO | WO 2013/110782 | 8/2013 | A61L 2/20 |

OTHER PUBLICATIONS

International Search Report and Opinion (English version only) from corresponding PCT/US15/21191; 6 pages, dated Jun. 4, 2015.

(Continued)

*Primary Examiner* — Donald Spamer
(74) *Attorney, Agent, or Firm* — Kusner & Jaffe; Michael A. Centanni

(57) ABSTRACT

A method for decontaminating an object disposed in a region. The method includes the steps of: heating the region to a target temperature; introducing steam into the region until a humidity level in the region reaches a target humidity level; introducing a vaporized sterilant into the region until a sterilant concentration in the region reaches a target sterilant concentration; and maintaining the target temperature, the target sterilant concentration and the target humidity level until a predetermine target dose is obtained.

16 Claims, 2 Drawing Sheets

(56) References Cited

U.S. PATENT DOCUMENTS

| | | | |
|---|---|---|---|
| 5,759,848 A * | 6/1998 | Nagoshi | C12Q 1/22 435/287.1 |
| 7,238,330 B2 | 7/2007 | Hill et al. | 422/292 |
| 8,007,717 B2 | 8/2011 | Hill | 422/3 |
| 8,129,579 B2 | 3/2012 | McVey et al. | 588/401 |
| 2005/0031486 A1 | 2/2005 | Mole et al. | 422/28 |
| 2007/0098592 A1 * | 5/2007 | Buczynski | A61L 2/208 422/3 |
| 2007/0292305 A1 | 12/2007 | Dempsey et al. | 422/28 |
| 2012/0219456 A1 | 8/2012 | Childers et al. | 422/28 |
| 2013/0230430 A1 | 9/2013 | Carbone et al. | 422/109 |

OTHER PUBLICATIONS

G. Fichet et al., "Prion inactivation using a new gaseous hydrogen peroxide sterilisation process," Journal of Hospital Infection (2007) 67, pp. 278-286.
Office Action issued in corresponding Australian Patent Application No. 2015231409 dated Oct. 21, 2016.

* cited by examiner

SATURATION-ENHANCED, LOW-CONCENTRATION VAPORIZED HYDROGEN PEROXIDE DECONTAMINATION METHOD

RELATED APPLICATIONS

This application claims the benefit of U.S. Provisional Application No. 61/955,283, filed on Mar. 19, 2014, which is fully incorporated herein by reference.

FIELD OF THE INVENTION

The present invention relates generally to disinfection and deactivation of rooms and regions.

BACKGROUND OF THE INVENTION

The use of vaporized hydrogen peroxide (VHP) is an established antimicrobial process. VHP is widely used to create sterile environments (clean rooms, etc.) and as a component of a contamination control method on sensitive equipment, in animal research labs, healthcare environments and the like. Recent developments have seen VHP considered for use on aircraft after an attack employing biological weapons. However, due to the rigorous requirements placed on aircraft components, there are concerns about the compatibility of the aircraft parts, substrates, adhesives, coatings, etc. with the VHP process. This is especially the case in modern 5th generation aircraft where composite materials are being used to replace many of the more traditional metal components.

The materials used in modern aircraft construction have strict limits on the temperature and other conditions to which they can be exposed. Typically, the aircraft must not be exposed to temperatures greater than 82° C. (180° F.) (the temperature an aircraft stored in direct sunlight at equatorial latitudes might reach).

To address the concern regarding the compatibility of aircraft parts with VHP, alternative methods have been developed to provide biological decontamination without exposing the aircraft to conditions (such as thermal stress) that might compromise the integrity of the materials of the aircraft. As used herein the term "decontamination" refers to the inactivation of bio-contamination, and includes, but is not limited to, sterilization and disinfection. One such method is referred to as Bio Thermal Decontamination (BTD). During a BTD process, an aircraft is heated to a temperature that is at or below the safe storage limit of the aircraft (e.g., about 82° C.) and exposed to high levels of humidity. These conditions have the same effect as steam sterilization and will cause inactivation of biological agents, including bacterial spores. However, because the temperature is low, as compared to a normal steam sterilization cycle (typically autoclaves operate at 120° C. or 130° C.), the time required for effective microbial inactivation is very long (many days).

Thus, there is a need for a decontamination process that provides effective microbial inactivation in a sensible time frame (hours not days) and that is compatible with the materials of modern aircraft.

SUMMARY OF THE INVENTION

In accordance with the present invention, there is provided a method for decontaminating an object disposed in a region. The method includes the steps of: heating the region to a target temperature; introducing steam into the region until a humidity level in the region reaches a target humidity level; introducing a sterilant into the region until a sterilant concentration in the region reaches a target sterilant concentration; and maintaining the target temperature, the target sterilant concentration and the target humidity level until a predetermined target dose is obtained.

In accordance with the present invention, it has been found that the addition of VHP to a BTD process causes microbial inactivation to occur rapidly at much lower temperatures and humidities, as compared to a standard BTD process, and at much lower VHP concentrations, as compared to a conventional VHP process. The addition of VHP to the BTD process results in cycle times that are unexpectedly short. By operating at a lower temperature and a lower humidity (i.e., at conditions far removed from the upper limits of compatibility for the aircraft materials), the continued airworthiness of the treated aircraft is ensured.

An advantage of the present invention is that the combination of modestly increased temperature, low humidity and a low concentration of VHP is capable of inactivating microorganisms much faster than a conventional BTD process, thereby allowing complete decontamination of an aircraft in a matter of hours rather than days or weeks.

An additional advantage of the present invention is that by operating at a modestly elevated temperature and low humidity it is much easier to operate a decontamination system. Operating at high temperatures and high humidities in a decontamination enclosure large enough to accommodate a whole aircraft is problematic. Such a system has a large energy consumption, and maintaining homogeneous temperature/humidity distribution is difficult.

Another advantage of the present invention is a process that is more compatible with the materials of modern aircraft.

A still further advantage of the present invention is a simplified system that is designed to have lower energy consumption, a simplified enclosure design, simpler insulation requirements, easier distribution of a sterilant, significantly faster decontamination times and the ability to quickly return the aircraft to service.

These and other advantages will become apparent from the following description of a preferred embodiment.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
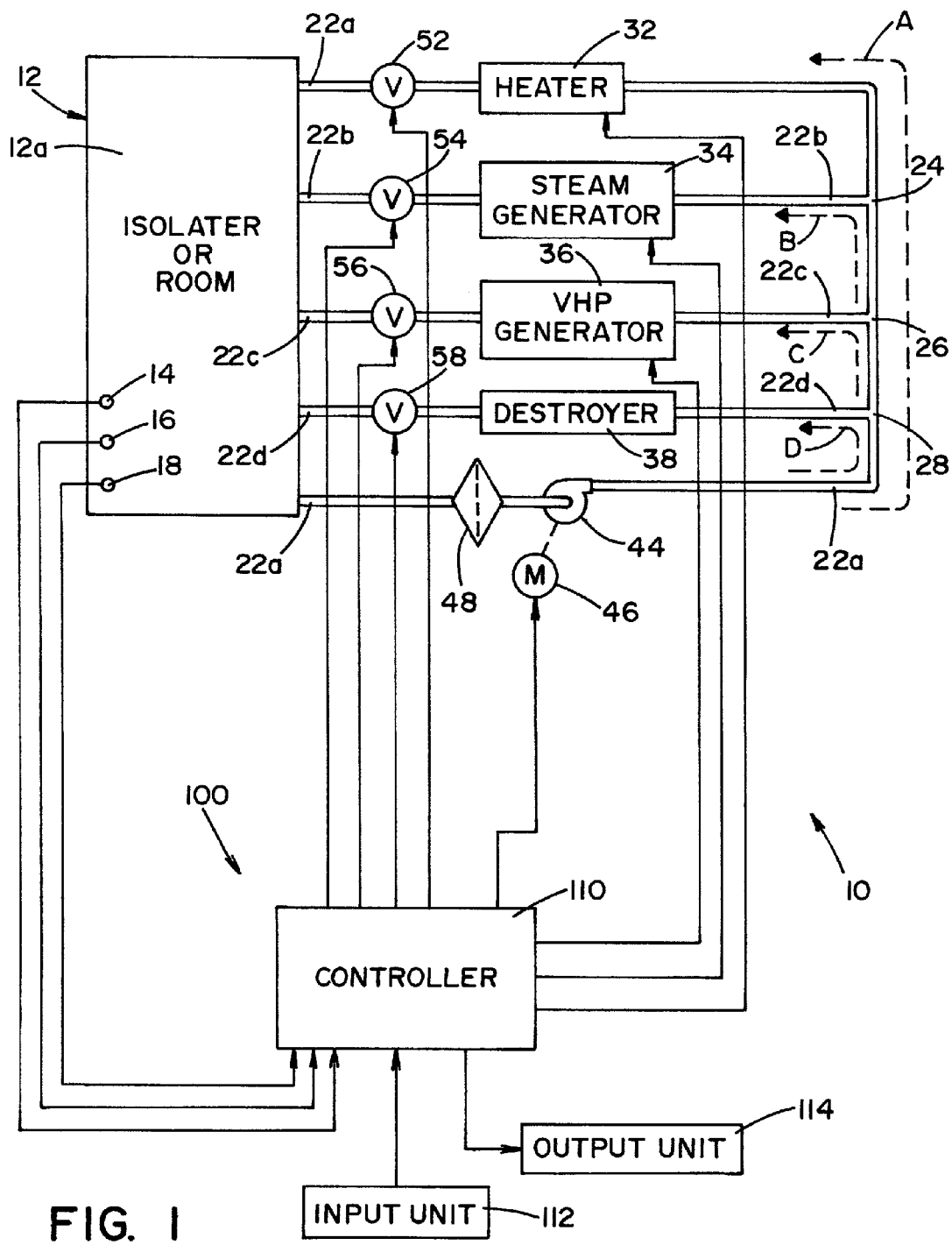
FIG. 1 is a schematic view of a sterilization system illustrating a preferred embodiment of the present invention.

Referring now to the drawings wherein the showings are for the purpose of illustrating a preferred embodiment of the invention only, and not for the purpose of limiting same, FIG. 1 shows a sterilization system 10, illustrating a preferred embodiment of the present invention. The present invention will be described with reference to using vaporized hydrogen peroxide (VHP) as a sterilant and combining VHP with humidity to disinfect or deactivate articles. However, it is contemplated that the sterilant may be one or more vaporous sterilants or a combination of one or more vaporous sterilants with one or more gaseous sterilants. By way of example and not limitation, the vaporous sterilant may include one or more of the following: peracetic acid, bleach and ammonia and the gaseous sterilant may include one or more of the following: ozone, chlorine dioxide, oxides of nitrogen and ethylene oxide. It is also contemplated that the sterilant may be one or more of the chemicals disclosed in U.S. Pat. No. 8,129,579 to McVey et al., hereby incorporated herein by reference.

System 10 includes an isolator or room 12 that defines an inner sterilization/decontamination chamber or region 12a. Articles to be sterilized or decontaminated may be disposed within isolator or room 12. It is contemplated that isolator or room 12 may be a tent or some other structure that is large enough to receive an aircraft.

A humidity sensor 14 is disposed within isolator or room 12. Humidity sensor 14 is operable to provide a variable electrical signal that is proportional to the humidity of the carrier gas within isolator or room 12.

A vaporized hydrogen peroxide (VHP) sensor 16 is disposed within isolator or room 12. VHP sensor 16 can be an electrochemical cell that gives a signal proportional to the concentration of VHP in isolator or room 12 or it can be a near infrared spectrophotometer that provides a similar signal or some other commercially available sensor for detecting the concentration of VHP in isolator or room 12.

A temperature sensor 18 is disposed within isolator or room 12. Temperature sensor 18 is operable to provide a variable electrical signal that is proportional to the temperature of the carrier gas within isolator or room 12.

System 10 is comprised of a first fluid flow path "A," a second fluid flow path "B," a third fluid flow path "C" and a fourth fluid flow path "D." First fluid flow path "A" is defined by isolator or room 12 and a first conduit 22a. One end of first conduit 22a connects to isolator or room 12. The other end of first conduit 22a also connects to isolator or room 12. In this respect, isolator or room 12 and first conduit 22a define a closed loop path.

Second fluid flow path "B" is defined by isolator or room 12, a portion of first conduit 22a and a second conduit 22b. One end of second conduit 22b connects to first conduit 22a at a junction 24. The other end of second conduit 22b connects to isolator or room 12. In this respect, isolator or room 12, a portion of first conduit 22a and second conduit 22b defined a closed loop path.

Third fluid flow path "C" is defined by isolator or room 12, a portion of first conduit 22a and a third conduit 22c. One end of third conduit 22c connects to first conduit 22a at a junction 26. The other end of third conduit 22c connects to isolator or room 12. In this respect, isolator or room 12, a portion of first conduit 22a and third conduit 22c defined a closed loop path.

Fourth fluid flow path "D" is defined by isolator or room 12, a portion of first conduit 22a and a fourth conduit 22d. One end of fourth conduit 22d connects to first conduit 22a at a junction 28. The other end of fourth conduit 22d connects to isolator or room 12. In this respect, isolator or room 12, a portion of first conduit 22a and fourth conduit 22d defined a closed loop path.

A heater 32 is disposed in first conduit 22a upstream of isolator or room 12 at a location between junction 24 and isolator or room 12. Heater 32 heats the carrier gas flowing along first fluid flow path "A." It is contemplated that heater 32 may be a conventional heater having electrical elements for heating the carrier gas conveyed therethrough. A first valve 52 is disposed in first conduit 22a upstream of isolator or room 12 at a location between heater 32 and isolator or room 12. First valve 52 regulates the flow of the carrier gas along first conduit 22a. First valve 52 is a variable flow valve.

A steam generator 34 is disposed in second conduit 22b. Steam generator 34 introduces steam into the carrier gas flowing along second fluid flow path "B." It is contemplated that steam generator 34 may be a conventionally known steam generator, such as the SA32 Vaporizer provided by STERIS Corporation for a small isolator or room 12 or, for a large isolator or room 12, a steam generator provided by Chromalox. A second valve 54 is disposed in second conduit 22b between steam generator 34 and isolator or room 12. Second valve 54 regulates the flow of the carrier gas along second conduit 22b. Second valve 54 is a variable flow valve.

A VHP generator 36 is disposed in third conduit 22c. VHP generator 36 introduces vaporized hydrogen peroxide into the carrier gas flowing along third fluid flow path "C." It is contemplated that VHP generator 36 may be a generator, such as the STERIS VHP 1000 ARD VHP Generation System, provided by STERIS Corporation for a small isolator or room 12, or a custom VHP generator, provided by STERIS Corporation. A third valve 56 is disposed in third conduit 22c between VHP generator 36 and isolator or room 12. Third valve 56 regulates the flow of the carrier gas along third conduit 22c. Third valve 56 is a variable flow valve.

A destroyer 38 is disposed in fourth conduit 22d. Destroyer 38 destroys the hydrogen peroxide ($H_2O_2$) in the carrier gas flowing along fourth fluid flow path "D." It is contemplated that destroyer 38 may be a catalylic destroyer made of a material that destroys VHP upon contact. A fourth valve 58 is disposed in fourth conduit 22d between destroyer 38 and isolator or room 12. Fourth valve 58 regulates the flow of the carrier gas along fourth conduit 22d. Fourth valve 58 is a variable flow valve.

A blower 44, driven by a motor 46, is disposed in first conduit 22a downstream of isolator or room 12 at a location between isolator or room 12 and junction 28. Blower 44 is designed to circulate a carrier gas simultaneously along first fluid flow path "A," second fluid flow path "B," third fluid flow path "C" and fourth fluid flow path "D." For a large isolator or room 12, blower 44 provides the carrier gas at a flow rate of between about 1,000 CFM and about 2,000 CFM. A filter 48 is disposed in first conduit 22a at a location upstream of blower 44. Filter 48 is operable to filter dirt and/or debris from the carrier gas circulated through first conduit 22a.

A control system 100 controls the operation of system 10. Control system 100 includes a controller 110 that controls the operation of motor 46, valves 52, 54, 56 and 58, heater 32, steam generator 34 and VHP generator 36. Controller 110 also monitors humidity sensor 14, VHP sensor 16, and temperature sensor 18. Controller 110 is a system microprocessor or a micro-controller that is programmed to control the operation of system 10. Controller 110 controls the flow position of first valve 52, second valve 54, third valve 56 and fourth valve 58 by providing an electronic signal to first valve 52, second valve 54, third valve 56 and fourth valve 58. Based on the selected flow position, first valve 52, second valve 54, third valve 56 and fourth valve 58 control the carrier gas flow rate along first fluid flow path "A,"

second fluid flow path "B," third fluid flow path "C" and fourth fluid flow path "D," respectively.

An input unit 112 is provided and attached to controller 110 to allow a user of system 10 to input operational parameters. Input unit 112 may be any device that would facilitate the input of data and information to controller 110 by a user of system 10, such as by way of example and not limitation, a keypad, a keyboard, a touch screen or switches.

An output unit 114 is also connected to controller 110. Output unit 114 is provided to enable controller 110 to provide information to the user regarding the operation of system 10. Output unit 114 may be, by way of example and not limitation, a printer, display screen or LED display. Controller 110 is programmed such that system 10 operates in predefined operating phases while maintaining certain preferable operating conditions.

Operation of System

The present invention shall now be further described with reference to the operation of system 10. A typical sterilization/decontamination cycle includes a heating phase, a decontamination phase and an aeration phase. Prior to the initiation of a sterilization/decontamination cycle, input unit 112 is used to provide the operational parameters to controller 110. The operational parameters may include target temperature(s) for the heating phase, the decontamination phase and the aeration phase, a target VHP concentration and a target humidity level for the decontamination phase, and a target VHP concentration for the aeration phase.

Heating Phase

When the sterilization/decontamination cycle is first initiated, controller 110 starts with the heating phase. Controller 110 positions first valve 52 in an open position and positions second valve 54, third valve 56 and fourth valve 58 in a closed position. Controller 110 also causes motor 46 to drive blower 44, thereby causing the carrier gas to circulate along first fluid flow path "A." During the heating phase, heater 32 is energized such that the temperature of the carrier gas in isolator or room 12 increases. Throughout the heating phase, temperature sensor 18 provides a signal to controller 110 that is proportional to the actual temperature of the carrier gas in isolator or room 12. Once the temperature in isolator or room 12 reaches the target temperature for the heating phase, controller 110 ends the heating phase. According to the present invention, the target temperature for the heating phase is between about 40° C. and about 60° C., preferably, between about 45° C. and about 55° C.

Decontamination Phase

Following the heating phase, the decontamination phase is then initiated. First valve 52 remains in the open position and controller 110 causes second valve 54 and third valve 56 to move to an open position to cause the carrier gas to flow along second fluid flow path "B" and third fluid flow path "C." The speed of motor 46 may be adjusted to provide the required flow along first fluid flow path "A," second fluid flow path "B" and third fluid flow path "C." Controller 110 will also control the positions of first valve 52, second valve 54 and third valve 56 to vary the flow rate of the carrier gas along the respective flow paths as required for correct system operation.

Controller 110 activates steam generator 34 and VHP generator 36 to provide steam and vaporized hydrogen peroxide, respectively, to isolator or room 12. In particular, steam generator 34 introduces steam into second fluid flow path "B" and the steam is carried by the carrier gas into chamber or region 12a of isolator or room 12. It is also contemplated that steam generator 34 may be connected directly to isolator or room 12, thereby simplifying the plumbing design and reducing the risk that the steam may condense prior to reaching isolator or room 12. Similarly, VHP generator 36 introduces vaporized hydrogen peroxide (VHP) into third fluid flow path "C" and the VHP is carried by the carrier gas into chamber or region 12a of isolator or room 12.

Throughout the decontamination phase, humidity sensor 14 provides a signal to controller 110 that is proportional to the humidity level in isolator or room 12, VHP sensor 16 provides a signal to controller 110 that is proportional to the VHP concentration in isolator or room 12 and temperature sensor 18 provides a signal to controller 110 that is proportional to the temperature in isolator or room 12. Throughout the decontamination phase, controller 110 periodically compares the actual humidity level, as measured by humidity sensor 14, to the target humidity, the actual VHP concentration, as measured by VHP sensor 16, to the target VHP concentration and the actual temperature, as measured by temperature sensor 18 to the target temperature. According to the present invention, the target humidity is at least about 50% relative humidity, preferably greater than about 60% relative humidity. Although higher humidity tends to increase the microbial inactivation rate during a decontamination process, the increased humidity also increases the likelihood that condensation may occur within isolator or room 12. Condensation may hinder proper disinfection of articles in isolation or room 12. Therefore, it is desirable to keep the humidity level below the level where condensation occurs. It is contemplated that controller 110 is programmed as disclosed in U.S. Pat. No. 8,007,717 to Hill, hereby incorporated herein by reference. U.S. Pat. No. 8,007,717 describes in detail a control method for regulating the concentration of a sterilant to prevent the occurrence of condensation during a sterilization/decontamination process.

The target VHP concentration for the present invention is between about 25 ppm and about 50 ppm. The present invention contemplates operating near 25 ppm to maximize the material compatibility aspect of the present invention.

Based on the measured humidity level, VHP concentration and temperature, controller 110 adjusts the operation of heater 32, steam generator 34 and VHP generator 36 and the position of first valve 52, second valve 54 and third valve 56 to maintain the target humidity, target VHP concentration and target temperature in isolator or room 12. For example, controller 110 is programmed to turn off heater 32 and cause first valve 52 to move to a closed position once the target temperature is reached in isolator or room 12. If the temperature within isolator or room 12 begins to fall below the target temperature, controller 110 is programmed to cause first valve 52 to move to a position to increase the flow of the carrier gas along first fluid flow path "A" and energize heater 32 to heat the carrier gas conveyed along first fluid flow path "A." Controller 110 is programmed to control the operation of steam generator 34, VHP generator 36, second valve 54 and third valve 56 to adjust the humidity level and the concentration of VHP in isolator or room 12 in a similar manner.

The decontamination phase continues until a predetermined "dose" has been obtained. The term "dose" is equivalent to the term "bioburden reduction," as used in U.S. Pat. No. 8,007,717 to Hill, hereby incorporated herein by reference. U.S. Pat. No. 8,007,717 describes in detail the control method for obtaining the predetermined "dose" of "bioburden reduction" based on measured VHP concentrations and humidity levels in isolator or room 12.

Aeration Phase

After the decontamination phase is completed, the aeration phase is initiated. Controller 110 de-energizes heater 32, steam generator 34 and VHP generator 36 to cease heating and introducing steam and VHP into isolator or room 12. Controller 110 then causes fourth valve 58 to move to the open position such that the carrier gas is conveyed along fourth fluid flow path "D" and through destroyer 38. Controller 110 maintains first valve 52, second valve 54 and third valve 56 in the open position such that the carrier gas is also conveyed along first fluid flow path "A," second fluid flow path "B" and third fluid flow path "C."

The aeration phase is run until the VHP concentration in isolator or room 12 is below the target VHP concentration for the aeration phase or below an allowable threshold (about 1 ppm). As can be appreciated, blower 44 continues to simultaneously circulate the carrier gas through first fluid flow path "A," second fluid flow path "B," third fluid flow path "C" and fourth fluid flow path "D," thereby causing the last of the vaporized hydrogen peroxide to be broken down by catalytic destroyer 38.

Figure 2:
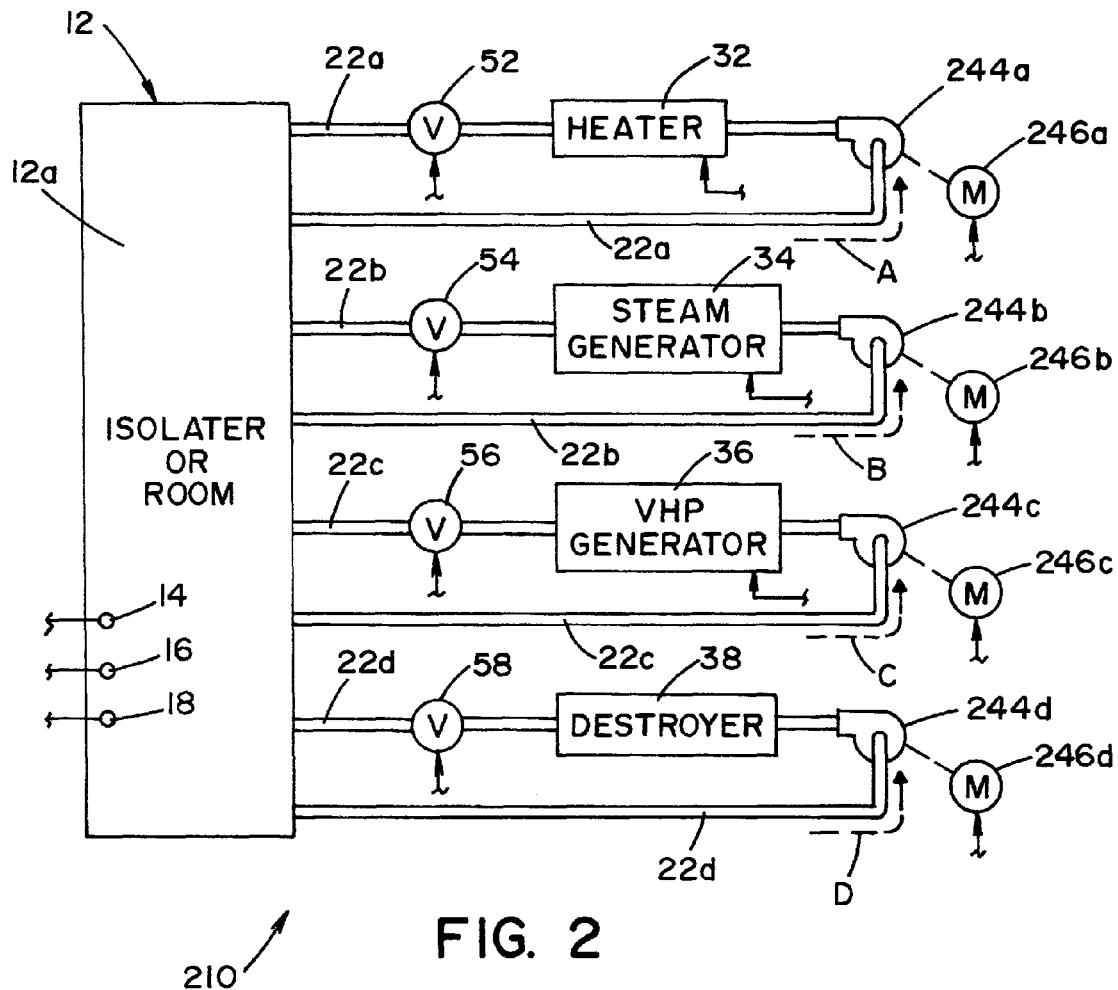
FIG. 2 is a schematic view of a sterilization system illustrating an alternative embodiment of the present invention with independent first, second, third and fourth fluid flow paths.

Referring now to FIG. 2, an alternative embodiment of the present invention, sterilization system 210, is shown. Components of system 210 that are similar to components of system 10 use like reference numbers. System 210 is similar to system 10, described above, except first fluid flow path "A," second fluid flow path "B," third fluid flow path "C" and fourth fluid flow path "D" are independent of each other. In particular, each fluid flow path includes a separate conduit and a separate blower for conveying the carrier gas along the respective fluid flow path. First fluid flow path "A" includes blower 244a driven by motor 246a, second fluid flow path "B" includes blower 244b driven by motor 246b, third fluid flow path "C" includes blower 244c driving by motor 246c and fourth fluid flow path "D" includes blower 244d driven by motor 246d. It is contemplated that one or more of first fluid flow path "A," second fluid flow path "B," third fluid flow path "C" and fourth fluid flow path "D" may include a filter for removing debris from the carrier gas circulated therethrough. Controller 110 (not shown) controls the operation of the components of system 210. The operation of system 210 is, in most respects, similar to the operation of system 10, as described above in detail. However, the four (4) independent fluid flow paths of system 210 allow for the use of smaller blowers while providing more independent control of each fluid flow path.

Test Setup

The following is a summary of tests performed to verify the operation of the present invention. The tests were conducted in a test chamber that was connected to a VHP 1000 ARD (manufactured by STERIS Corporation) to provide VHP to the test chamber. The test chamber was also connected to a modified SA32 Vaporizer (manufactured by STERIS Corporation) to provide steam to the test chamber. A space heater was provided to heat the carrier gas in the test chamber.

A plurality of biological indicators (BI's) was placed in the test chamber to determine the log reduction for each test run. The BI's were Tri scale Bacillus thuringiensis Biological Indicators, produced by Mesa Labs. During each test, six (6) BI's were placed in the chamber in various locations, e.g., taped to walls of the chamber or suspended, using strings, into a central portion of the chamber.

For each test, the chamber was sealed and the temperature in the chamber was raised to a target temperature using the space heater. Once at the target temperature, steam and VHP were injected using the SA32 Vaporizer, and the VHP1000 ARD, respectively, to raise the humidity and the concentration of VHP to the desired set points. A total dose of VHP during the cycle was calculated and aeration was started once a target dose was attained.

Test Results

Table 1 contains test data showing how the combination of reduced Bio Thermal Decontamination (BTD) conditions with small amounts of VHP provides an efficient sterilization/decontamination process with enhanced material compatibility. The term "BDL" stands for "below detection limit." In the present test runs, the BDL is ~4 log. The term "NA" refers to data that are not available. A log reduction of 7.20 is the largest log reduction possible based on the type of inoculum used on the biological indicators.

TABLE 1

Log Reduction Results

| Test Run | Temp (° C.) | [VHP] (ppm) | Humidity (%) | Dose Set Point (ppm*min) | Log Reduction |
|---|---|---|---|---|---|
| 1 | 38 | 50 | 50 | 1500 | BDL |
| 2 | 38 | 50 | 80 | 1500 | 6.26 |
| 3 | 38 | 50 | 50 | 2100 | NA |
| 4 | 38 | 50 | 80 | 2100 | NA |
| 5 | 49 | 25 | 50 | 1500 | 4.48 |
| 6 | 49 | 25 | 80 | 1500 | 7.20 |
| 7 | 49 | 25 | 50 | 2100 | 7.20 |
| 8 | 49 | 25 | 80 | 2100 | 7.20 |
| 9 | 43 | 25 | 40 | 1800 | BDL |
| 10 | 43 | 25 | 90 | 1800 | 7.20 |
| 11 | 43 | 25 | 65 | 1295 | 6.26 |
| 12 | 43 | 25 | 65 | 2305 | 7.20 |
| 13 | 34 | 25 | 65 | 1800 | 6.26 |
| 14 | 53 | 25 | 65 | 1800 | 7.20 |
| 15 | 43 | 25 | 65 | 1800 | 7.20 |
| 16 | 43 | 25 | 65 | 1800 | 7.20 |
| 17 | 43 | 25 | 65 | 1800 | 7.20 |
| 18 | 43 | 25 | 65 | 1800 | 7.20 |
| 19 | 43 | 25 | 65 | 1800 | 7.20 |
| 20 | 43 | 25 | 65 | 1800 | 7.20 |

Initial testing (i.e., Runs 1, 2, 3 and 4) was conducted using a VHP concentration of 50 ppm. Inspection of these results clearly illustrates the impact of humidity on log reduction. For example, increasing the humidity level in an enclosure from 50% to 80% results in a significant increase in log reduction, i.e., from <4 log to 6.3 (see Runs 1 and 2, respectively). All further testing was conducted at 25 ppm since the goal of this testing was to determine efficacy at low concentrations of VHP.

Because the majority of the test runs resulted in complete inactivation of all BI's (i.e. no growth of all BI's incubated), a detailed statistical analysis of the data collected would be inconclusive. However, inspection of the data results in the following observations:

A comparison of Runs 9, 11 and 15 (see Table 2) illustrates the impact of increased humidity on log reductions. Run 9 (40% humidity) results in a log reduction that is below the detection limit. However, at an increased humidity level (i.e., 65%) and a lower total dose (see Run 11) a greater than 6 log reduction is achieved. Similar trends were observed between Runs 5 and 6 (see Table 3).

TABLE 2

Data and Set Points for Runs 9, 11 and 15

| Test Run | Temp (° C.) | [VHP] (ppm) | Humidty (%) | Dose Set Point (ppm*min) | Log Reduction |
|---|---|---|---|---|---|
| 9 | 43 | 25 | 40 | 1800 | BDL |
| 11 | 43 | 25 | 65 | 1295 | 6.26 |
| 15 | 43 | 25 | 65 | 1800 | 7.20 |

TABLE 3

Data and Set Points for Runs 5 and 6

| Test Run | Temp (° C.) | [VHP] (ppm) | Humidity (%) | Dose Set Point (ppm*min) | Log Reduction |
|---|---|---|---|---|---|
| 5 | 49 | 25 | 50 | 1500 | 4.48 |
| 6 | 49 | 25 | 80 | 1500 | 7.20 |

Table 4 illustrates the significance of temperature on log reduction. Runs 11 and 13 were run at 43° C. and 34° C. respectively, and show the same log reduction even though the dose for Run 11 (1295 ppm*min) is significantly lower than the dose for Run 13 (1800 ppm*min). In other words, Runs 11 and 13 show that, for a predetermined log reduction, the required dose decreases as the temperature of the sterilization/decontamination process increases.

TABLE 4

Data and Set Points for Runs 11 and 13.

| Test Run | Temp (° C.) | [VHP] (ppm) | Humidity (%) | Dose Set Point (ppm*min) | Log Reduction |
|---|---|---|---|---|---|
| 11 | 43 | 25 | 65 | 1295 | 6.26 |
| 13 | 34 | 25 | 65 | 1800 | 6.26 |

Table 5 illustrates the cycles times for several test runs. As shown in Table 5, the total cycle time for the tests was 84 minutes or less, i.e., significantly less than the cycle times for the BTD process (i.e., on the order of days).

TABLE 5

Cycle Time Results for Selected Test Runs

| Test Run | Temp (° C.) | [VHP] (ppm) | Humidity (%) | Dose Set Point (ppm*min) | Log Reduction | Cycle Time (mins.) |
|---|---|---|---|---|---|---|
| 1 | 38 | 50 | 50 | 1500 | BDL | 44 |
| 2 | 38 | 50 | 80 | 1500 | 6.26 | 49 |
| 3 | 38 | 50 | 50 | 2100 | NA | 57 |
| 4 | 38 | 50 | 80 | 2100 | NA | 63 |
| 5 | 49 | 25 | 50 | 1500 | 4.48 | 68 |
| 9 | 43 | 25 | 40 | 1800 | BDL | 84 |
| 11 | 43 | 25 | 65 | 1295 | 6.26 | 64 |
| 13 | 34 | 25 | 65 | 1800 | 6.26 | 80 |

The present invention, thus, provides a method for efficiently decontaminating an object, e.g., a modern aircraft, in a sensible time frame (hours not days) and in a manner that is compatible with the materials of the aircraft.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method for decontaminating an object disposed in a region, said method comprising the steps of:
heating said region to a target temperature by introducing heat via a heated carrier gas into said region to increase a temperature in said region to said target temperature and maintain said temperature in said region at said target temperature, said heated carrier gas being heated outside of said region by a heater positioned within a heater conduit leading to said region; and
decontaminating said region by simultaneously controlling respective introduction of the heat, steam, and a vaporized sterilant into said carrier gas that is respectively circulated into said region through the heater conduit, a steam conduit, and a vaporized sterilant conduit, each of said conduits being positioned outside said region and part of a circulating loop by which said carrier gas circulated into said region returns to said conduits, the heat, the steam, and the vaporized sterilant being introduced into said region until a predetermined target dose of said vaporized sterilant is administered to said object, said heat being introduced into said region when said temperature of said region falls below said target temperature until said temperature in said region reaches said target temperature, said steam being introduced into said region when said target temperature is initially reached and a relative humidity level in said region is below a target humidity level until said relative humidity level in said region reaches said target humidity level, said vaporized sterilant being introduced into said region when a sterilant concentration in said region is below a target sterilant concentration until said sterilant concentration in said region reaches said target sterilant concentration,
wherein said target sterilant concentration is between about 25 ppm and about 50 ppm, said target temperature is between about 40° C. and about 60° C. and said target humidity level is greater than about 50% relative humidity.

2. A method as defined in claim 1, wherein said target sterilant concentration is about 25 ppm.

3. A method as defined in claim 1, wherein said object is an aircraft.

4. A method as defined in claim 1, wherein said predetermined target dose is about 2300 ppm-min or less.

5. A method as defined in claim 1, wherein said sterilant is vaporized hydrogen peroxide.

6. A method as defined in claim 1, wherein said sterilant includes one or more vaporized sterilants.

7. A method as defined in claim 6, wherein said vaporized sterilants includes one or more of the following: vaporized hydrogen peroxide, peracetic acid, bleach and ammonia.

8. A method as defined in claim 6, wherein said sterilant includes one or more gaseous sterilants.

9. A method as defined in claim 8, wherein said gaseous sterilant includes one or more of the following: ozone, chlorine dioxide, oxides of nitrogen and ethylene oxide.

10. A method as defined in claim 1, wherein said introduction of said heat, said steam, and said vaporized sterilant into said carrier gas is controlled in view of respective sensor feedback from said region.

11. A method as defined in claim 1, further comprising:
aerating said region after said predetermined target dose of said vaporized sterilant is administered to said object during said decontamination, said region being aerated until a sterilant concentration in said region falls below said target sterilant concentration, the aerating comprising:
  ceasing introduction of said heat, said steam, and said vaporized sterilant into said carrier gas; and
  controlling a destroyer positioned outside said region in a destroyer conduit to break down said vaporized sterilant in said carrier gas, said destroyer being part of the circulating loop by which said carrier gas circulated into said region returns to said conduits.

12. A method for decontaminating an object disposed in a region, said method comprising:
  heating said region to a target temperature, the heating comprising:
    circulating a carrier gas along a first fluid flow path defined by said region and a first conduit, the first conduit having ends that are each connected to said region; and
    controlling a heater disposed in said first conduit to introduce heat into said first fluid flow path to be carried by said circulating carrier gas into said region to heat said region to said target temperature;
  decontaminating said object after heating said region to said target temperature, the decontaminating comprising:
    circulating said carrier gas along said first fluid flow path, a second fluid flow path, and a third fluid flow path, said second fluid flow path being defined by said region, a portion of said first conduit that receives said carrier gas from said region, and a second conduit, said third flow path being defined by said region, said carrier gas receiving portion of said first conduit, and a third conduit, said second and third conduits extending from said region to said carrier gas receiving portion of said first conduit;
    controlling said heater to maintain said target temperature in said region during said decontamination;
    controlling a steam generator disposed in said second conduit to introduce steam into said second fluid flow path to be carried by said circulating carrier gas into said region to humidify said region to a target humidity level and maintain said target humidity level during said decontamination;
    controlling a sterilant generator disposed in said third conduit to introduce vaporized sterilant into said third fluid flow path to be carried by said circulating carrier gas into said region to reach a target sterilant concentration and maintain said target sterilant concentration during said decontamination;
  aerating said region after a predetermined target dose of said vaporized sterilant is administered to said object during said decontamination, said region being aerated until a sterilant concentration in said region falls below said target sterilant concentration, the aerating comprising:
    de-energizing said heater, said steam generator, and said sterilant generator;
    circulating said carrier gas along said first fluid flow path, said second fluid flow path, said third fluid flow path, and a fourth fluid flow path, said fourth fluid flow path being defined by said region, the carrier gas receiving portion of said first conduit, and a fourth conduit, said fourth conduit extending from said region to said carrier gas receiving portion of said first conduit; and
    controlling a destroyer disposed in said fourth conduit to break down said vaporized sterilant contained in said circulating carrier gas.

13. A method as defined in claim 12, wherein said vaporized sterilant is vaporized hydrogen peroxide (VHP).

14. A method as defined in claim 12, wherein said target sterilant concentration is between about 25 ppm and about 50 ppm,
  wherein said target temperature is between about 40° C. and about 60° C., and
  wherein said target humidity level is greater than about 50% relative humidity.

15. A method as defined in claim 12, wherein said predetermined target dose is about 2300 ppm-min or less.

16. A method as defined in claim 12, wherein said object is an aircraft.

* * * * *